Figure 1:
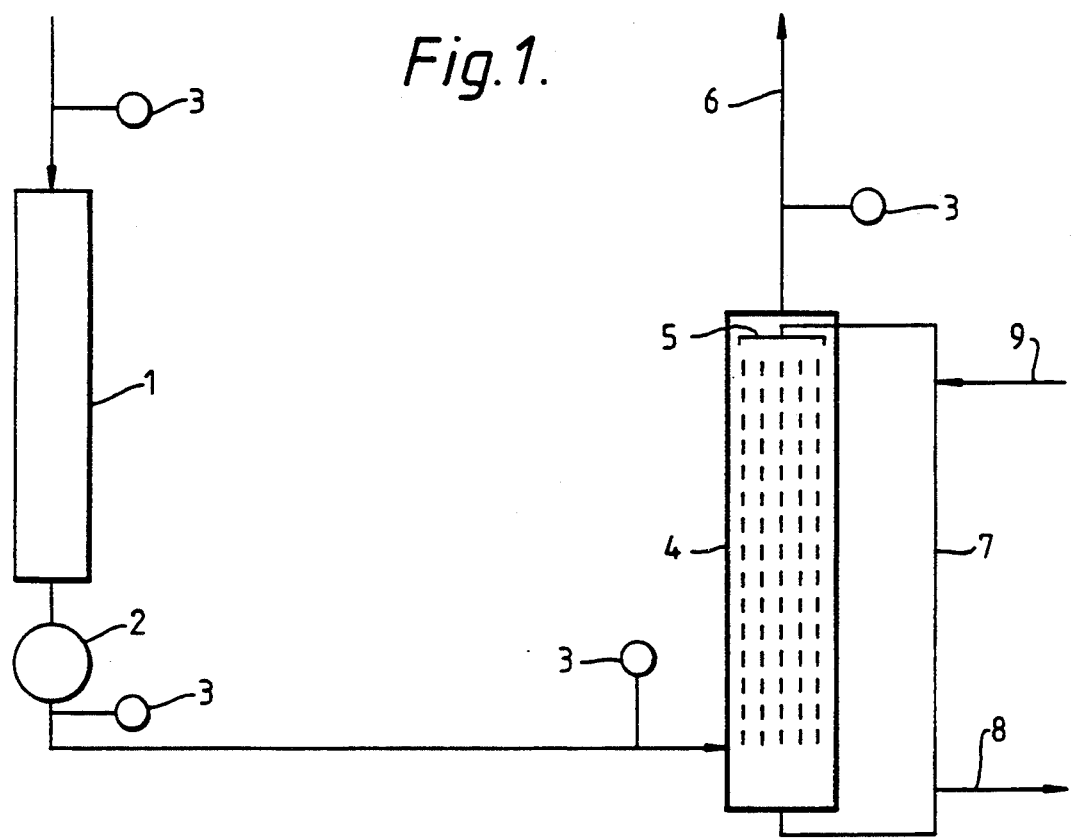

United States Patent [19]

Jennings et al.

[11] Patent Number: 5,336,791
[45] Date of Patent: Aug. 9, 1994

[54] PRODUCTION OF ETHYLENE OXIDE

[75] Inventors: James R. Jennings, Yarm; Percy Hayden, Hutton Meadows, both of England

[73] Assignee: Imperial Chemical Industries PLC, London, England

[21] Appl. No.: 955,725
[22] PCT Filed: Jun. 18, 1991
[86] PCT No.: PCT/GB91/00976
   § 371 Date: Feb. 19, 1992
   § 102(e) Date: Feb. 19, 1992
[87] PCT Pub. No.: WO91/19706
   PCT Pub. Date: Dec. 26, 1991

[30] Foreign Application Priority Data

Jun. 19, 1990 [GB] United Kingdom ............ 9013662
Apr. 8, 1991 [GB] United Kingdom ............ 9107345

[51] Int. Cl.$^5$ ............ C07D 301/10; C07D 301/32; C07D 303/04
[52] U.S. Cl. ............ 549/538; 549/523; 549/534
[58] Field of Search ............ 549/538, 534, 523

[56] References Cited

U.S. PATENT DOCUMENTS 4,822,900  4/1989  Hayden ............ 549/538
4,822,926  4/1989  Dye ............ 568/867

FOREIGN PATENT DOCUMENTS 3642     8/1979  European Pat. Off. .
176253   4/1986  European Pat. Off. .

*Primary Examiner*—Joseph E. Evans
*Attorney, Agent, or Firm*—Cushman, Darby & Cushman

[57] ABSTRACT

A gas stream from a reaction in which ethylene oxide is produced by reacting ethylene with oxygen which gas stream comprises oxides of nitrogen and steam the gas stream is contacted with an aqueous alkaline quench solution and ethylene oxide is then recovered from the gas stream. A substantial amount of oxides of nitrogen is removed from the gas stream during the treatment with the quench solution.

9 Claims, 1 Drawing Sheet

PRODUCTION OF ETHYLENE OXIDE

This invention relates to the production of ethylene oxide.

It is known front U.S. Pat. No. 4,822,926 to produce ethylene oxide by reacting ethylene with oxygen in the presence of a silver containing catalyst and a chlorine containing reaction modifier in the absence of nitrate and/or nitrite forming substances in the gas phase and to spray the gas stream flowing from the reactor with aqueous alkali. This cools the gas stream and removes impurities such as oxalic acid, aldehydes and aldol products. Some ethylene oxide is inevitably removed and at least partly hydrolysed to ethylene glycol during this step.

It is also known from European Patent No 0003642 that ethylene may be oxidised with oxygen to ethylene oxide in the presence of a silver containing catalyst and a nitrate or nitrite forming substance which is in the gas phase simultaneously with a chlorine containing reaction modifier. The gas stream from the reaction generally comprises unreacted materials, impurities, $H_2O$, oxides of nitrogen and other gases as well as ethylene oxide.

The oxides of nitrogen, though not dangerous in themselves tend to react with other components derived from the reaction in subsequent purification sections of process plant to produce solid or liquid organic nitrogen compounds which may accumulate in cold parts and represent an explosion hazard and/or contaminate the product of the process.

We have found that a significant proportion of the oxides of nitrogen can be removed by contacting the gas stream flowing from the reactor with aqueous alkali prior to recovery of the ethylene oxide from the reaction gas stream.

Accordingly, this invention provides a process in which a gas stream from a reaction in which ethylene oxide is produced by reacting ethylene with oxygen which gas stream comprises oxides of nitrogen and steam is treated by contacting it with an aqueous alkaline quench solution, thereby removing nitrogen oxides and/or organic nitrogen containing compounds from the gas stream, and subsequently recovering ethylene oxide from the gas stream.

The accompanying FIG. 1 is a diagrammatic illustration of apparatus and process for carrying out the invention.

The stream of reaction gas is treated with an aqueous alkaline quench solution. Prior to the contact with the quench solution there is no substantial condensation of water from the gas stream. Suitably the gas stream is contacted with 0.01 to 5% and preferably 0.05 to 0.5% of its own volume of an alkali solution, for example a sodium and/or potassium hydroxide end/or carbonate solution, preferably having a pH of 7.1 to 9.5 and more preferably 7.5 to 9 as finely divided droplets with a residence time of the gas 0.05 to 30 seconds. Contacting with a stream of aqueous alkali may also be carried out by passing the gas stream through the liquid for example as such or as liquid flowing over porous packing. The temperature of the stream of aqueous alkaline quench liquid is suitably 10° C. to 40° C. The temperature of the gas stream at the start of the treatment with the aqueous alkaline quench solution is typically from 50° C. to 100° C. The quench additionally serves the purpose of cooling the reaction gas to a temperature of typically 20° C. to 50° C., close to the temperatures typically used in ethylene oxide absorbers.

The oxides of nitrogen may comprise NO, $NO_2$, $N_2O_4$, $N_2O_3$ and/or $N_2O_5$ and organic nitrogen containing compounds can include compounds such as nitromethane, 2-nitroethanol and nitroethylene.

We have found that this procedure is effective to remove a surprisingly high proportion of the nitrogen containing compounds, particularly the inorganic nitrogen containing compounds, in the gas stream. It is further effective to remove the formaldehyde that can be formed by homogenous reactions in the stream of reaction gas in the presence of nitrogen oxides. The quench thus serves an additional purpose in at least reducing the amount of formaldehyde reaching the ethylene oxide removal stage. Separation of ethylene oxide and formaldehyde once they are both in solution in water is a difficult and/or expensive step e.g. involving specialised distillation equipment.

The reaction gases will typically contain from 0.1 to a few hundred parts per million and usually at most 50 parts per million, for sample 0.5 to 30 parts per million by volume of oxides of nitrogen, the treatment with the aqueous alkaline quench need cause little hydration and loss of ethylene oxide. Below 50 parts per million of the reaction gas by volume the loss of ethylene oxide is small.

Suitably the reaction gas stream is cooled from a reaction temperature of for example 190° to 280° C. and particularly 210° to 270° C. to from 50° C. to 100° C. prior to contact with the quench solution. The temperature of the gas stream is not reduced so far as to cause any significant amount of water to condense from the gas stream prior to contact with the quench solution.

The aqueous stream from the quench may be heated as a liquid to cause reaction of ethylene oxide contained in it to ethylene glycol suitably at a temperature of 150° to 230° C. and preferably 170° to 210° C. and subsequently distilled in one or more stages to recover pure mono ethylene glycol and optionally di- and higher ethylene glycols from it. In the course of this treatment oxides of nitrogen and organic nitrogen compounds tend to react to form heavy nitrogen containing residues which are easily separated. Any light nitrogen containing species which may be present are also readily removed in the distillation.

The alkali solution may be recirculated to the contact stage thereby increasing their content of ethylene oxide and glycol, improving their suitability for treatment as aforesaid to recover ethylene glycol. It may be necessary to add further alkaline materials to such recirculated solution to compensate for the absorbtion of the nitrogen oxides. The removal of formaldehyde, and possibly other organic materials such as acetaldehyde, from the reaction gas stream, may lead to a build up of such organic materials in the recycled solution and this may also assist in the removal of oxides of nitrogen.

Subsequently, ethylene oxide can then suitably be removed from the reaction gas stream conventionally by absorption into water and description to recover the ethylene oxide. The water is preferably re-used in the absorption stage several times and used water treated for recovery of ethylene glycol and its oligomers and polymers. The gas after removal of ethylene oxide may be treated to remove at least part of the carbon dioxide produced as a by product of the process and recycled to the process.

The reaction producing ethylene oxide may be carried out as described in European Patent Specification 0003642 which is incorporated herein by reference. The nitrate or nitrite forming compounds described therein other than oxides of nitrogen are converted at least in part to oxides of nitrogen in the process, and this my be at least to some extent part of the mechanism by which nitrates and nitrites are formed in the process.

The following Example illustrates the invention. All percentages and parts per million (ppm) of gas streams are by volume.

EXAMPLE 1

One form of the invention will now be described with reference to the accompanying FIG. 1.

Ethylene oxide reactor 1 feeds a cooler 2 from which a pipe passes to alkali contactor 4, which comprises means to spray an aqueous alkaline solution through incoming gas 5 and means to remove sprayed gas 6 and means 7 to recover alkali solution and to recycle part thereof together with fresh solution to the alkali contactor, part of the used alkali solution is purged through purge line 8. Sample points 3 are provided in appropriate positions. Fresh alkali is added through line 9.

A gas stream comprising:

| | |
|---|---|
| Ethylene | 30% |
| Oxygen | 6.5% |
| Carbon Dioxide | 1% |
| Methane | 62.5% |
| Ethyl Chloride | 5 ppm |
| $NO/NO_2$ | 12 ppm |
| Water Vapour | 25 mm Hg (approx) (ca. 3.3 kPa) | was fed to reactor 1 at a rate of 48 $m^3.hr^{-1}$ and at a pressure of 15 bar and the reactor was held at an average temperature of 234° C. The reactor contained 9 liters of a catalyst comprising silver supported on porous α-alumina pellets.

The gas flowing from the reactor contained 2.1% of ethylene oxide, 0.8% of steam and 9.7 parts per million oxides of nitrogen and about 95 mm Hg (ca. 12.7 kPa) pressure of water vapour. The selectivity of the reaction under these conditions, expressed as moles of ethylene oxide produced per hundred moles of ethylene consumed, was 87%. The temperature of the gas stream was reduced to between 80° and 100° C. in the cooler. The gas stream was passed to the alkali contactor through the pipe and the temperature of the gas fell to 60*** at the inlet to the alkali contactor 4. No condensation of liquid water was observed prior to the entry of the gas stream into the alkali contactor.

The alkali contact solution had a pH of 8 to 8.5, the alkali being added intermittently as 1% sodium hydroxide in an amount sufficient to maintain the pH in that range with rejection of a corresponding amount of recovered alkali solution. The solution was sprayed through the gas at a rate of 140 liters per hour. The purged alkali quench solution comprised organic and inorganic nitrogen containing compounds in a ratio of 1.1:1 and represented 48% of the total nitrogen oxide fed to the reactor.

We claim:

1. A process in which a gas stream from a reaction in which ethylene oxide is produced by reacting ethylene with oxygen which gas stream comprises oxides of nitrogen and steam is treated by contacting it with an aqueous alkaline quench solution, thereby removing nitrogen oxides and/or organic nitrogen containing compounds from the gas stream, and subsequently recovering ethylene oxide from the gas stream.

2. A method as claimed in claim 1 wherein the quench solution is an alkali solution of sodium and/or potassium hydroxide and/or carbonate having a pH of 7.1 to 9.5.

3. A method as claimed in claim 1 wherein the volume of quench solution is 0.01 to 5% of the volume of the reaction gas stream.

4. A method as claimed in claim 1 wherein the residence time of the reaction gas stream with the quench solution is from 0.05 to 30 seconds.

5. A method as claimed in claim 1 wherein the stream of reaction gas is contacted with the quench solution by spraying the quench solution into the stream of reaction gas in the form of of finely divided droplets.

6. A method as claimed in claim 1 wherein the stream of reaction gas is contacted with the quench solution by passing the gas stream through the solution flowing over porous packing.

7. A method as claimed in claims 1, 2, 3, 4, 5 or 6 wherein the temperature of the stream of aqueous alkaline quench liquid is 10° C. to 40° C.

8. A method as claimed in any one of claims 1, 2, 3, 4, 5 or 6 wherein the temperature of the gas stream at initial contact with the aqueous alkaline quench solution is from 50° to 100° C.

9. A method as claimed in claim 1 wherein the gas stream is cooled from a reaction temperature of from 190° to 280° C. to a temperature of from 50° to 100° C. prior to contact with the aqueous alkaline quench solution.

* * * * *